United States Patent [19]

Lloyd et al.

[11] Patent Number: 4,593,686
[45] Date of Patent: Jun. 10, 1986

[54] MONITOR FOR AN ANTI-APNEA DEVICE

[76] Inventors: Stephen R. Lloyd, 5642 N. Bernard, Chicago, Ill. 60659; Charles F. Samelson, 5712 S. Kenwood, Chicago, Ill. 60637

[21] Appl. No.: 670,991
[22] Filed: Nov. 13, 1984
[51] Int. Cl.⁴ .............................................. A61F 5/56
[52] U.S. Cl. ................................... 128/136; 430/573
[58] Field of Search ............... 128/136; 430/573–576
[56] References Cited

U.S. PATENT DOCUMENTS

| | | | |
|---|---|---|---|
| 3,480,010 | 11/1969 | Crossley | 128/136 |
| 3,566,387 | 2/1971 | Schoener et al. | 340/573 |
| 4,169,473 | 10/1979 | Samelson | 128/136 |
| 4,178,589 | 12/1979 | Nunn et al. | 128/136 |
| 4,304,227 | 12/1981 | Samelson | 128/136 |

Primary Examiner—Kyle L. Howell
Assistant Examiner—David Shay
Attorney, Agent, or Firm—Norman Lettvin

[57] ABSTRACT

A monitor system is provided for a device used in the treatment of sleep apnea. The device engages the user's tongue in a socket. The tongue is thereby held in a forward position, increasing the size of the air passageway, while at the same time flow of air through the mouth is blocked. The monitor is responsive to the position of the tongue in the socket and activates an alarm when the tongue slips out of the socket. One example of such a monitor includes circuitry with a thermistor. Thermistor temperature changes are used to generate a voltage that enables alarm and recording circuitry.

16 Claims, 5 Drawing Figures

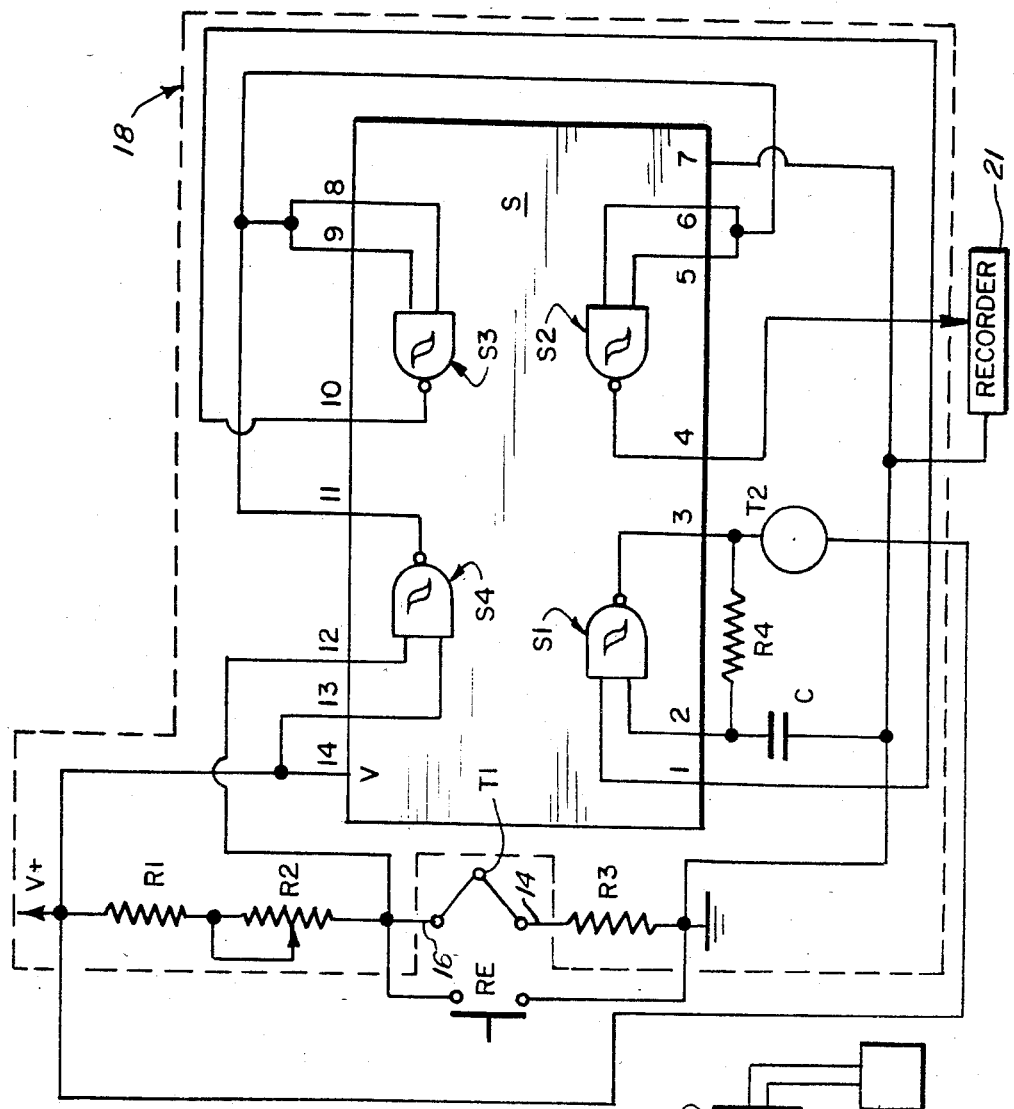
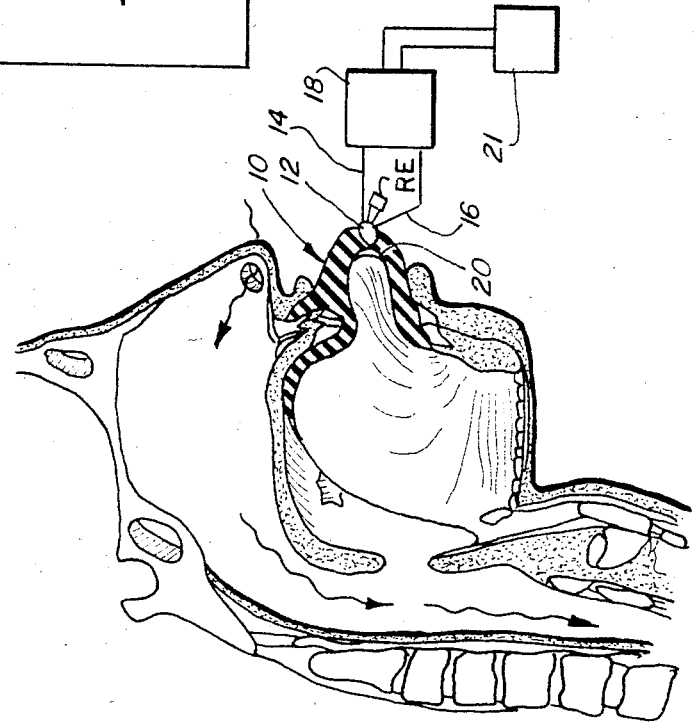
FIG. 2
FIG. 1

ABSTRACT# MONITOR FOR AN ANTI-APNEA DEVICE

This invention relates to apparatus for the treatment of sleep apnea syndrome and/or snoring. More particularly, this invention relates to a tongue retaining device and a sensor for monitoring the use of the device.

BACKGROUND OF THE INVENTION

Sleep apnea is an illness characterized by cessation of breathing during sleep. An apnea episode has been defined as a period of 10 seconds or greater duration of no respiration. See Cartwright, R.D. et al., "The Effects of a Nonsurgical Treatment for Obstructive Sleep Apnea," J. Am. Med. Ass'n 248, p. 705 (1982). After onset of an apnea episode, sleep typically lightens to the point where breathing resumes after 10 to 180 seconds, or the patient may wake up. Patients usually remain unaware of their sleep apneas, even though they may awaken as many as several hundred times each night. Episodes of repeated sleep apneas may take up practically the entire night.

C. F. Samelson, U.S. Pat. Nos. 4,169,473 and 4,304,227, incorporated herein by reference, discloses a device for prevention of obstructive sleep apnea and snoring. When the device is operatively positioned within the mouth, flow of air through the mouth is blocked. A socket within the device engages the tip of a user's tongue, holding the tongue in a forward position. Positive engagement of the tongue in the socket results when the user creates a negative pressure condition within the socket by applying a gentle suction in the socket which operates to hold the tip of the tongue in the socket. The body of the tongue, when so engaged, is held forward of its normal proximity to the soft palate, the uvula and the posterior pharyngeal wall, thereby providing an increase in size of the air passageway through which breathing occurs.

The anti-apnea device described in U.S. Pat. No. 4,304,227 could be expelled from the patient's mouth during sleep, or suction may be lost during sleep, so that the user's tongue slips out of the socket. Protection against sleep apnea and snoring is lost in either event.

SUMMARY OF THE INVENTION

An object of the present invention is to monitor the proper operative engagement of a user's tongue within the socket of a device of the type disclosed in U.S. Pat. No. 4,304,227.

The present invention also features an alarm system for waking a sleeping user of the patented tongue holding device when the device ceases to provide the desired protection against sleep apnea.

These and other objects, advantages, and features of the invention will become readily apparent from the following detailed description of a preferred embodiment, which is presented in conjunction with the accompanying drawings.

BRIEF DESCRIPTION OF THE DRAWINGS

FIG. 1 illustrates a monitor exemplifying principles derived from the present invention, located in place on an anti-apnea device holding a tongue in position.

FIG. 2 illustrates an exemplary detector circuit as used with a thermistor for thermal detection of tongue position in the monitor shown in FIG. 1.

DETAILED DESCRIPTION OF A PREFERRED EMBODIMENT

Figure 4:
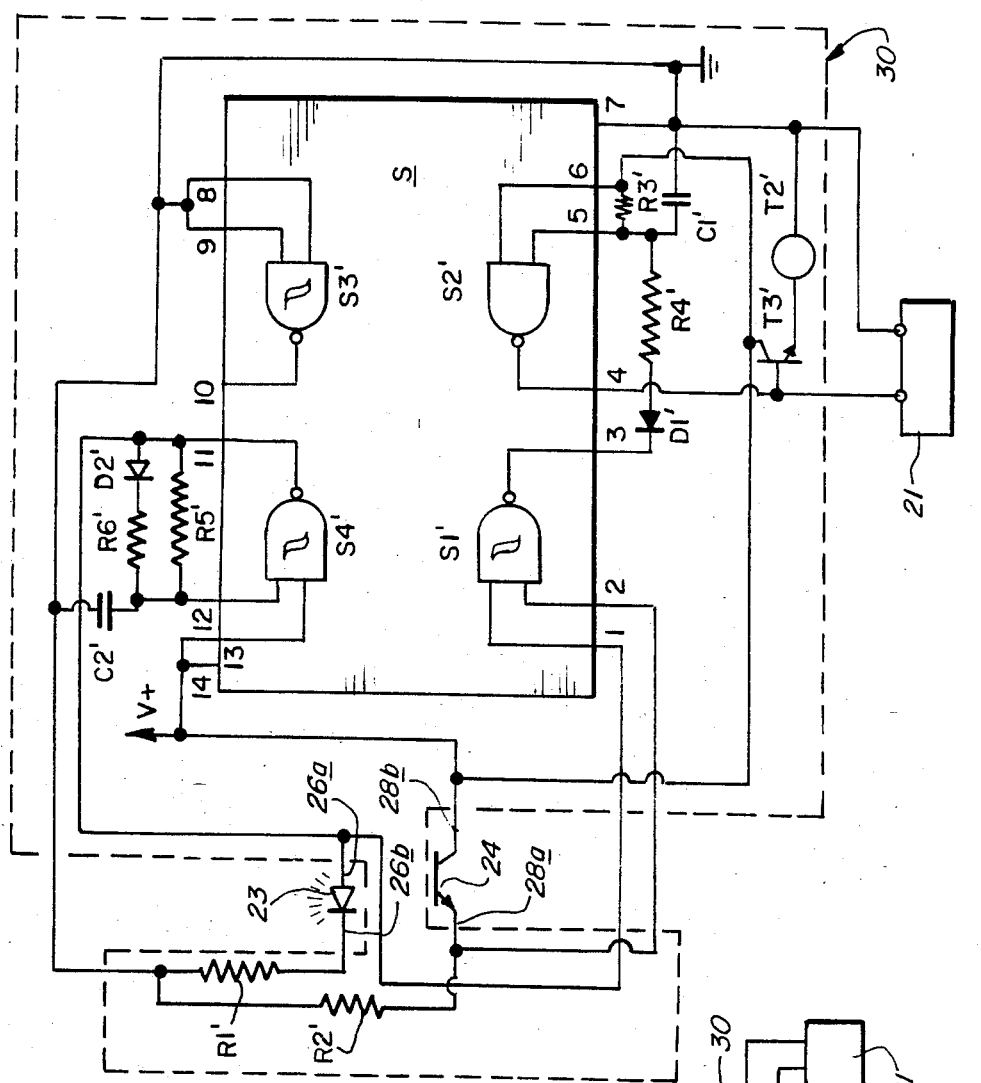
FIG. 4 illustrates an exemplary detector circuit for use with the optical system shown in FIG. 3.

As illustrated in FIG. 1 an anti-apnea device 10 may be equipped with a monitor comprising a sensor 12 connected by leads 14, 16 to a detector 18. The anti-apnea device 10 is shown in cross section in FIG. 1 as it would appear installed in a human mouth holding the tongue in a forwardly extended position.

The sensor 12 is responsive to the presence of the tip of the tongue within a tongue retaining socket 20 of the anti-apnea device 10. Suction sensitive switches, pressure transducers, temperature transducers such as thermistors, light and photocell combinations and capacitance measuring devices all provide examples of sensors 12 that may be used within the scope of the present invention. Other sensors, not specifically mentioned herein, may also be used. The detector 18 may provide a bistable output which assumes a first state when the sensor 12 indicates the presence of the tongue within the tongue retaining socket 20 and a second state when the tongue is absent. The detector 18 may then provide an alarm when it is in the second state. The term "alarm" should not be construed to be limited to audible alarms, such as an audio transducer operatively coupled to an audio frequency oscillator, but refers generally to any means of generating a stimulus sufficient to awaken a sleeping person. Therefore audible alarms, visible alarms such as flashing lights, and devices to provide electrical or vibratory stimuli all provide examples of alarms that may be used within the scope of the present invention. The detector 18 may be monitored by a recording monitor 21 in a different room from the monitor.

It is not necessary that the detector 18 monitor the presence of the tongue in the socket continuously. It is necessary only that the detector 18 check for the engagement of the tongue in the tongue retaining socket 20 with sufficient frequency to ensure that the anti-apnea device 10 provides the desired protection against sleep apnea and snoring. For example, checking for the presence of the tongue once every few seconds is as adequate as continuous monitoring.

Accordingly, in a device for treatment of sleep apnea by preventing the flow of air through a user's mouth while engaging the tip of the user's tongue in a socket, the engagement resulting from creation of suction in the socket, an improvement may comprise:
detection means for generating an electrical signal when the tongue is disengaged from the socket; and
alarm means operably coupled to the detection means for generating an alarm in response to the electrical signal.

The detection means may comprise an exemplary detector circuit suitable for use with a thermistor sensor T1 as illustrated in FIG. 2.

The thermistor is positioned in the anti-apnea device 10, as illustrated in FIG. 1, to respond to temperature changes in the tongue retaining socket 20. The tongue retaining socket 20 is heated to a higher temperature, by the tongue's presence, when the tongue is present than when the tongue is retracted from the tongue retaining socket. The thermistor T1 resistance correspondingly decreases as the thermistor temperature increases. One lead of the thermistor T1 is connected to a DC voltage source V+ through a fixed resistor R1 and a variable resistor R2. The remaining lead from the thermistor T1 is connected to ground through a resistor R3. The high voltage side of the thermistor T1 is also connected to ground through a reset switch RE which is normally open and must be manually operated. The DC voltage source supplying voltage V+ is connected to pins S-13 and S-14 of a quad 2-input NAND Schmitt trigger chip S. Pin S-14 is the positive voltage supply V and pin S-13 connects to a first input of NAND gate S4 of chip S. Pin S-12 connects to the high voltage side of thermistor T1. It may be thereby be seen that NAND gate S4 is used as a Schmitt trigger comparator.

The output S-11 of NAND gate S4 is connected to both input terminals S-8 and S-9 of NAND gate S3 which thereby may be seen to function as an inverter. The output from pin S-10 connects to one input S-1 of NAND gate S1. The output from pin S-3 of NAND gate S1 is connected to the remaining input S-2 through resistor R4. A capacitor with capacitance C is connected between pin S-2 and ground. It may be seen that gate S1 together with the feedback resistor R4 and the capacitor C comprises a gated oscillator. The output of the gated oscillator intermittently enables an alarm T2 which may comprise a driver circuit and a piezoelectric buzzer. Alternatively, T2 may be an audio frequency oscillator coupled to an audio transducer, a flashing light, or means for applying a slight electrical shock to wake the user of the anti-apnea device 10.

The output S-11 of NAND gate S4 also connects to the two inputs S-5 and S-6 of NAND gate S2. The output from pin S-4 of NAND gate S2, which may be seen to be substantially the inverted output from NAND gate S4, provides a monitor output to the recording monitor 21. The recording monitor 21 provides a continuous indication of the tongue's presence within the tongue retaining socket 20.

In one exemplary construction of the monitor, using a thermistor element, typical component values may be chosen in accordance with Table I.

TABLE I

| R1 ... 1 MΩ | | R4 ... 430KΩ |
|---|---|---|
| R2 ... 500KΩ | potentiometer | C ... 1 μf |
| R3 ... 2 MΩ | | |

Here chip S is a CD4093 device manufactured by National Semiconductor Corporation. Thermistor T1 is a Type FT 51J1-WC, manufactured by Fenwall Electronics.

The input voltage to pin S-12 is set at slightly less than the voltage level at which a transition of the output of gate S4 at pin S-11 occurs, changing the output from a high to a low. The voltage is controlled by the variable resistor R2, with the tongue in place within the tongue retaining socket 20 near the thermistor T1. Because of the presence of the tongue the thermistor temperature is relatively high and resistance correspondingly low. With the output from pin S-11 in a high state the input at pin S-1 is low, and the output from pin S-3 is a stable high. At the same time the monitor output from gate S2 at pin S-4 is a low.

If, on the other hand, the tongue slips out of place then the resistance of the thermistor T1 increases, causing the voltage at pin S-12 to increase past the transition threshhold. The output at pin S-11 is thereby forced into a low state. As a result, the input at pin S-1 of gate S1 switches high. At the time the input pin S-1 switches high the input pin S-2 is also high so that the output at pin S-3 switches low. When pin S-3 switches to a low state the gate S2, with the associated resistor R4 and capacitor C, begins to oscillate at a frequency of approximately 3 Hz. The output from pin S-3 thereby pulse modulates an audible signal from the alarm T2. The output pin S-4 of gate S2 also goes high, signalling the recording monitor 21 that the tongue is no longer present within the tongue retaining socket 20.

Closing of the reset RE grounds the pin S-12 input to NAND gate S4 which has the effect of forcing the oscillator S1 into its stable high state forcing monitor pin S-4 low. If the tongue is in place in the socket, the oscillator will remain in its stable state after release of the reset RE, and pin S-4 will remain low.

An alternate construction that embodies principles of the present invention may make use of a pressure transducer within the tongue retaining socket 20 of the mask in place of the thermistor 12. The pressure transducer senses the slight suction holding the tongue in place within the tongue retaining socket 20. An exemplary transducer and associated circuitry has been disclosed in S. K. Gupta, "Solid State Barometer" in *Radio Electronics* (June 1984) pp. 41–44, incorporated herein by reference. A comparator and alarm system, operably connected to the circuitry disclosed by Gupta, would provide a construction embodying the desired inventive principles.

Figure 3:
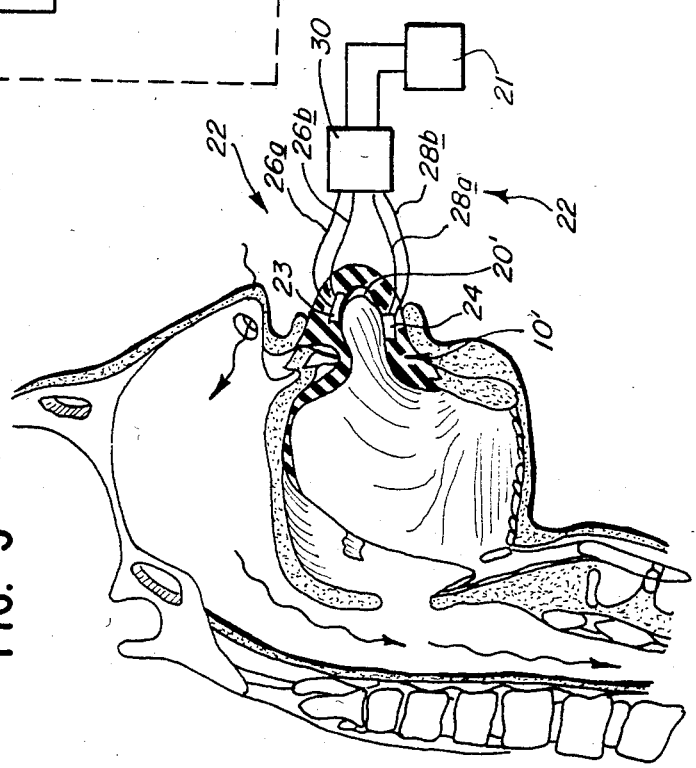
FIG. 3 illustrates a second alternate construction of the monitor illustrated in FIG. 1, showing an optical system for detecting presence of the tongue in the desired position.

An exemplary second alternate construction that embodies principles of the present invention includes an optical system 22, as illustrated in FIG. 3. The optical system 22 includes a light-emitting diode, or LED 23, and a photodetector 24 mounted on opposite sides of the tongue retaining socket 20' of the anti-apnea device 10'. Pairs of leads 26a, 26b and 28a, 28b, respectively, connect LED 23 and photodetector 24 to an interrogating pulse detector 30.

The interrogating detector 30, illustrated in FIG. 4, may also be constructed using a quad 2-input NAND Schmitt trigger chip S'. The detector 30 includes 3 gates of the quad chip S' connected to function as a pulsed voltage supply S4', a NAND gate S1', and a pulse detector S2'. The pulsed voltage supply S4' provides for periodic activation of LED 23, rather than continuous activation, in order to conserve battery power. The output from NAND gate S1' goes low only when light from the activated LED 23 strikes the phototransistor 24 during the active period of LED 23, which would indicate absence of the tongue from the tongue retaining socket 20. The pulse detector S2' detects the resulting low-going pulse and responds with a high output which activates the recorder 21 and activates alarm T2' by turning on switching transistor T3'.

Output pin S'-11 of gate S4', which supplies a train of voltage pulses, is connected to the "p" side of LED 23, the "n" side of which is connected to ground through resistor R1'. Pin S'-11 is also connected to enabling pin S'-1 of NAND gate S1'. The high voltage supply V+ is connected to the collector of phototransistor 24, the emitter of which is connected to ground through resistor R2'. The emitter is also connected to input pin S'-2 of NAND gate S1'.

The output pin S'-3 of NAND gate S1' remains high when LED 23 is activated by a voltage pulse from pin S'-11 and no light is detected by the phototransistor 24, because pin S'-2 remains substantially at ground voltage. No detection of light by the phototransistor 24 corresponds to the tongue being present in the tongue retaining socket 20. If, on the other hand, the tongue is absent, then the phototransistor 24 will detect a light pulse when a voltage pulse is applied to LED 23. The light pulse causes the phototransistor 24 to conduct, and current flow through resistor R2' raises the voltage on pin S'-2. The raised voltage at pin S'-2 is coincident with the voltage pulse from pin S'-11, which is applied to pin S'-1 of gate S1', thereby causing pin S'-3 to go low to substantially ground voltage.

The high voltage supply is also connected to pin S'-6 of pulse detector gate S2' and to pin S'-5 by resistor R3'. Capacitor C1' is connected between ground and pin S'-5, and the values of R3' and C1' are chosen to have a time constant of the order of the voltage cycle time of oscillator gate S4'. Pins S'-5 and S'-6 are therefore both normally high during operation, and output pin S'-4 is normally low. Pin S'-4 is connected to the base of switching transistor T-3' which is connected between the high voltage supply V+, on the collector side, and the alarm T2' on the emitter side. Transistor T3' is therefore normally off.

Pin S'-4 is also connected to 21, the low indicating normal operation of the tongue retaining device, i.e., indicating that the tongue is held within the retaining socket 20.

Pin S'-5 is connected to NAND gate output pin S'-3 by resistor R4' in series with diode D1', the diode being forward biased when pin S'-3 is low. When pin S'-3 is pulsed low, indicating absence of the tongue from the tongue retaining socket 20, the capacitor C1' rapidly discharges through resistor R4' and diode D1'. Pin S'-5 thereby is driven low and pin S'-4 goes high, turning on transistor T3' to activate alarm T2'. The high on pin S'-4 also signals an abnormal condition to the recording monitor 21. Continuing low pulses from pin S'-3 keep capacitor C1' discharged and maintain the high output from Pin S'-4 while the tongue is absent from the tongue retaining socket 20.

The pulsed voltage supply S4' is obtained by connecting input pin S'-13 to the high voltage supply V+ and output pin S'-11 to input pin S'-12 through resistor R5' in parallel with series connected resistor R6' and diode D2'. Diode D2' is forward biased when S'-11 is high and S'-12 is low. A capacitor C2' is connected between pin S'-12 and ground. Resistor R6' has a much smaller resistance than resistor R5'. Accordingly, when pin S'-12 is low, pin S'-11 is high and current flows principally through diode D2' and resistor R6', rapidly charging capacitor C2' and raising the voltage on pin S'-12. When the voltage on pin S'-12 rises above the up-down transition threshold, pin S'-11 goes low. Capacitor C2' then discharges slowly through resistor R5' until the voltage on pin S'-12 falls below the down-up transition threshold, and pin S'-11 goes high to start another cycle.

Use of 2-input NAND Schmitt triggers is not a necessary feature of the present invention. For example, similar circuitry to that illustrated in FIG. 4 may be constructed using single input Schmitt triggers such as comprise the CD 40106 integrated circuit.

The pulsed voltage supply described in connection with FIG. 4 may also be used in connection with other embodiments. For example, the embodiment illustrated in FIG. 2 could be built with a pulsed voltage supply in order to consume less power than would be consumed in continuous operation.

Typical component values for the second alternate construction of FIGS. 3 and 4 are shown in Table II.

TABLE II

| | |
|---|---|
| R1' ... 390Ω | R5' ... 2.2 MΩ |
| R2' ... 510KΩ | R6' ... 2.2KΩ |
| R3' ... 2.2 MΩ | C1' ... .47 μf |
| R4' ... 2KΩ | C2' ... 1 μf |

The diodes are 1N914"s. Chip S' is a CD4093. T3' is a Radio Shack Cat. No. 276-2009 npn transistor available from Radio Shack, 300 One Tandy Center, Ft. Worth, TEX 76102. The LED and phototransistor are sold by Radio Shack under Catalogue No. 276-42, operating in the infrared. With the stated component values, the pulsed voltage supply operates with a period of about 1 sec, providing voltage pulses with a width of about 10 msec.

Figure 5:
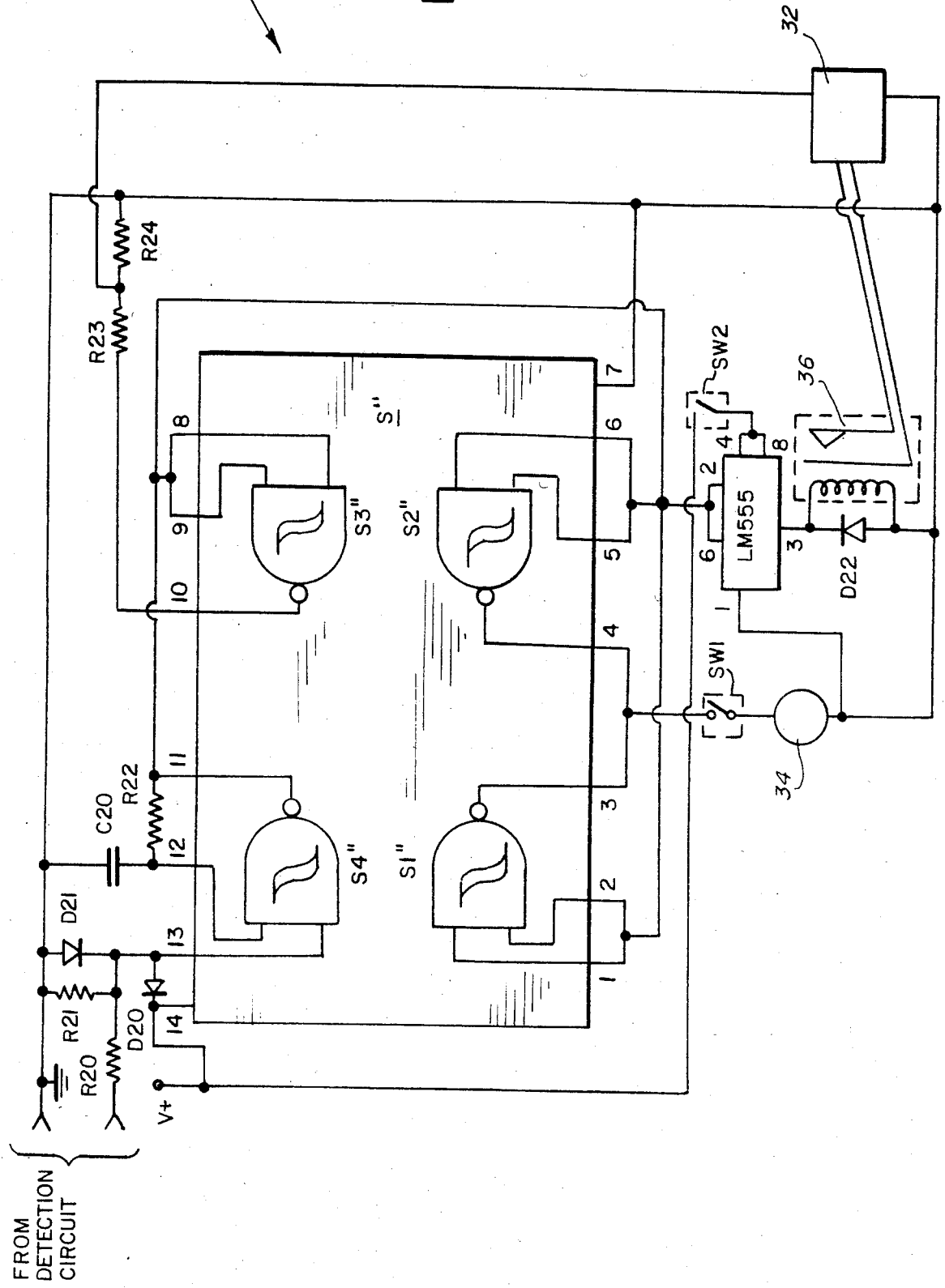
FIG. 5 illustrates circuitry for a recorder system for use with the detector circuits shown in FIGS. 2 and 4.

Circuitry for an exemplary recording monitor 21, using a quad 2-input NAND Schmitt trigger chip S", is illustrated in FIG. 5. The input to the recorder from pin S-4 in FIG. 2 or S'-4 in FIG. 4 connects to pin S"-13 through input resistor R20. Reverse biased diodes D20, and D21 are connected, respectively, from pin S"-13 to the high voltage at pin S"-14 and to ground to provide voltage limiting protection to input pin S"-13. Pull-down resistor R21 maintains input pin S"-13 at ground potential when there is no input connection. The ground in FIG. 5 is common with that in FIGS. 2 or 4.

Feedback resistor R22 is connected between the S4" output pin S"-11 and the second input pin S"-12. Capacitor C20 is connected between input pin S"-12 and ground. Accordingly, when the input at pin S"-13 through resistor R20 is low, gate S4" outputs a stable high at pin S"-11. When the input is high, on the other hand, gate S4" outputs an oscillating voltage in the same fashion as the gate S1 in FIG. 2.

The output from pin S"-11 is connected to pins S"-8 and S"-9 of gate S3" which functions as an inverter. The output from gate S3" at pin S"-10 goes to ground through a voltage divider comprising resistors R23 and R24 in series. The divided voltage is then input to one channel of a multi-channel pen recorder 32. Voltage division is necessary because the output at pin S"-10 is normally much too large for input to most pen recorders.

The output from pin S"-11 is also connected to the two inputs S"-5, S"-6 of gate S2" and the two inputs S"-1, S"-2 of gate S1". The respective output pins S"-3 and S"-4 are connected together and to the input of a piezo-buzzer 34 through a switch SW1. The gates S1" and S2", operating in parallel, thereby provide sufficient current to drive the buzzer 34 when an oscillating voltage appears at pin S"-11. The switch SW1 provides for disabling of the buzzer.

The output from pin S"-11 is also connected to pins 555-2 and 555-6 of an LM555 integrated circuit timer connected to operate as an inverting relay driver. Accordingly, pins 555-4 and 555-8 are connected to the high voltage at pin S"-14 through switch SW2. Pin 555-1 is grounded, and output pin 555-3 is connected to drive a relay 36. Clamping diode D22 is connected across the relay input terminals to protect the LM 555 from reverse voltage spikes generated by the relay coil each time the relay is turned off. The relay 36 is connected to the recorder 32 and, when activated, causes the recorder 32 to record fiducial marks. Switch SW2 provides means for disabling the relay.

Typical component values for the recording monitor 21 are shown in Table III.

TABLE III

| R20 ... 10KΩ | R23 ... 51KΩ |
|---|---|
| R21 ... 1 MΩ | R24 ... 10KΩ |
| R22 ... 910KΩ | C20 ... 1 µf |

Diodes D20 and D21 are 1N914's, diode D22 is a 1N4001. Chip S" is a CD4093. With the stated component values the cycle time is about 1 sec.

It will, of course, be understood that modification of the present invention in its various aspects will be apparent to those skilled in the art, some being apparent only after study and others being a matter of routine design. Monitors such as are described herein may be used with other anti-apnea devices than the exemplary device disclosed in the Samelson patents. Further, the use of the particular components described herein are not necessary features of the present invention. Other sensors and circuits will also be in keeping with principles taught by the present invention. For example, the LED-phototransistor combination of FIG. 3 may be replaced with a pair of capacitor plates attached to a circuit to measure the resonant frequency of the capacitor and a suitably disposed inductor, the resonant frequency depending upon the tongue's presence or absence. Also, the particular circuits disclosed herein may be readily adapted for use with other sensors by persons having ordinary electronic skills. Accordingly, the scope of the invention should not be limited by the particular embodiments and specific constructions herein described, but should be defined only by the appended claims and equivalents thereof.

What is claimed is:

1. In a device for treatment of sleep apnea by preventing the flow of air through a user's mouth while engaging the tip of the user's tongue in a socket, the engagement resulting from creation of suction in the socket, the improvement comprising:
   detection means connected to the device for generating an electrical signal when the tongue is disengaged from the socket; and
   alarm means operably coupled to said detection means for generating an alarm in response to said electrical signal.

2. In a device for treatment of sleep apnea by preventing the flow of air through a user's mouth while engaging the tip of the user's tongue in a socket to hold the tongue in a forward position within the mouth, the engagement resulting from tongue created suction in the socket, the improvement comprising:
   a detection system operatively coupled to the socket and responsive to the engagement of the user's tongue within the socket,
   an alarm system having an alarm state and a stable state, operatively coupled to said detection system, the operative coupling causing the alarm system to be in the stable state when the tongue is within the socket and in the alarm state when the tongue is not within the socket.

3. A device in accordance with claim 2 wherein said detection system includes a temperature transducer.

4. A device in accordance with claim 3 wherein said temperature transducer includes a thermistor.

5. A device in accordance with claim 2 wherein said detection system includes a pressure transducer.

6. A device in accordance with claim 2 wherein said alarm system includes an audio frequency oscillator operatively coupled to an audio transducer.

7. A device in accordance with claim 2 wherein said alarm system includes a NAND gate Schmitt trigger oscillator.

8. A device in accordance with claim 7 wherein said alarm system includes a piezo-electric buzzer driven by said Schmitt trigger oscillator.

9. A device in accordance with claim 2 wherein said alarm system includes means for applying electrical shock stimulus to a sleeping person.

10. A device in accordance with claim 2 wherein said alarm system includes means for applying vibratory stimuli to a sleeping person.

11. A device in accordance with claim 2 wherein said alarm system includes a flashing light.

12. A device in accordance with claim 2 wherein said detection system includes a light emitting diode and phototransistor.

13. A device in accordance with claim 12 wherein said alarm system includes an interrogating pulse detector.

14. A device in accordance with claim 13 wherein said interrogating detector includes a pulsed voltage supply, a pulse detector and an alarm gate.

15. A device in accordance with claim 2 further including a recording monitor operatively coupled to said alarm system for monitoring and recording the state of said alarm system.

16. A device in accordance with claim 15 wherein said recording monitor includes a circuitry for driving a multichannel pen recorder.

* * * * *